Figure 1:
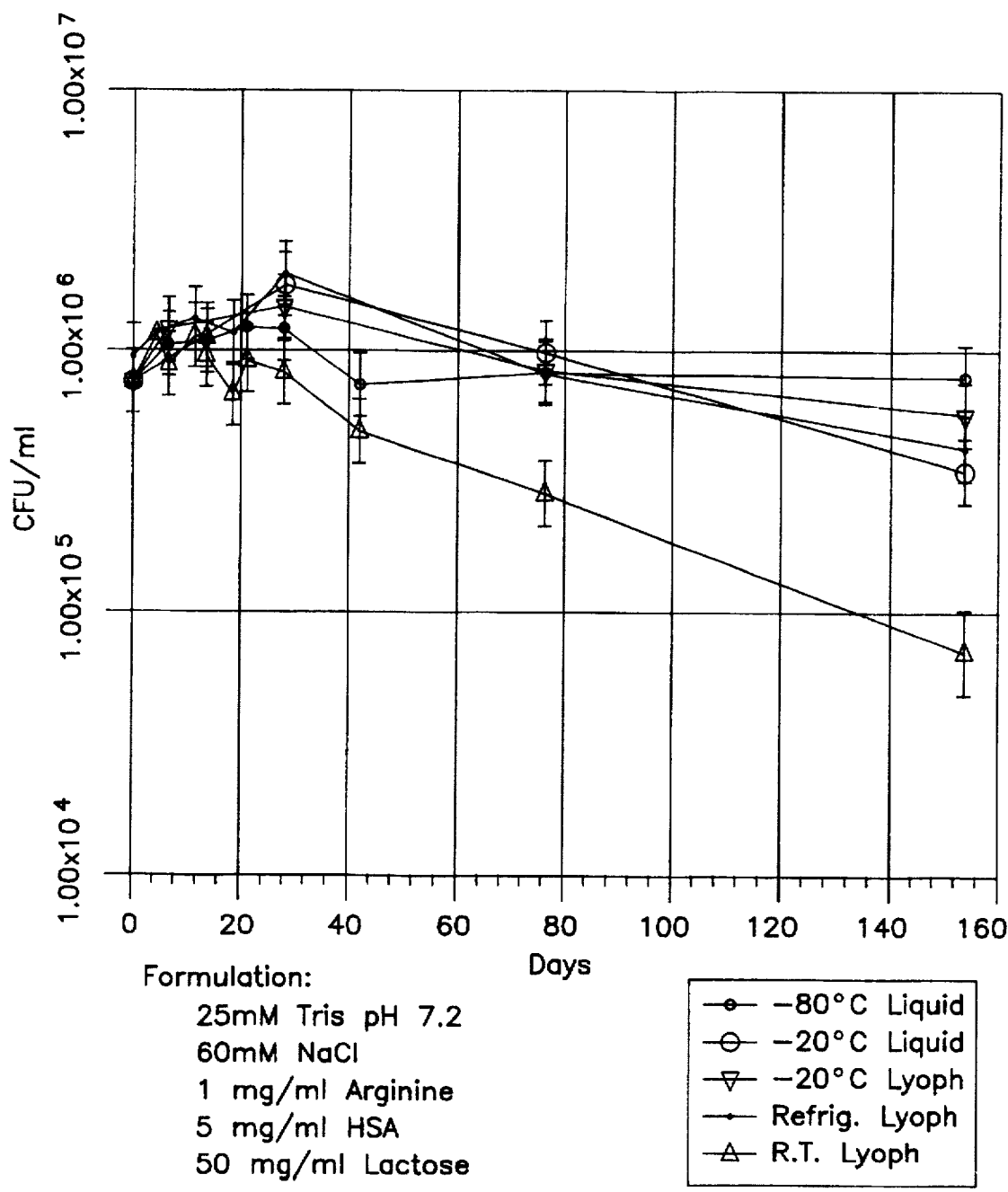

United States Patent [19]
Herrmann et al.

[11] Patent Number: 5,792,643
[45] Date of Patent: Aug. 11, 1998

[54] METHODS FOR PRESERVING RECOMBINANT RETROVIRUSES

[76] Inventors: Steven M. Herrmann, 836 Essence Ave., Ocean Side, Calif. 92057; Charles E. Prussak, 3905 Torrey Hill La., San Diego, Calif. 92130

[21] Appl. No.: 825,415

[22] Filed: Mar. 28, 1997

Related U.S. Application Data

[63] Continuation of Ser. No. 602,165, Feb. 16, 1996, abandoned, which is a continuation of Ser. No. 153,342, Nov. 15, 1993, abandoned, which is a continuation-in-part of Ser. No. 135,938, Oct. 12, 1993, abandoned.

[51] Int. Cl.⁶ ................................................ C12N 1/04
[52] U.S. Cl. .................. 435/235.1; 435/260; 435/320.1
[58] Field of Search ........................ 435/172.3, 235.1, 435/239, 243, 260, 320.1

[56] References Cited

U.S. PATENT DOCUMENTS

| | | | |
|---|---|---|---|
| 3,915,794 | 10/1975 | Zygraica et al. | 435/235.1 |
| 4,132,775 | 1/1979 | Volenec et al. | 424/89 |
| 4,338,335 | 7/1982 | McAleer et al. | 517/777 |
| 4,380,582 | 4/1983 | Orlando et al. | 435/239 |
| 4,500,512 | 2/1985 | Barme | 424/89 |
| 4,859,587 | 8/1989 | Roizman | 435/69.3 |

FOREIGN PATENT DOCUMENTS

| | | |
|---|---|---|
| 030199 | 5/1981 | European Pat. Off. |
| 0252059 | 1/1988 | European Pat. Off. |
| 0334530 | 9/1989 | European Pat. Off. |
| 0520748 | 6/1992 | European Pat. Off. |
| 2076787 | 10/1971 | France |
| 2201079 | 4/1974 | France |
| 2111829 | 7/1983 | United Kingdom |

OTHER PUBLICATIONS

Moritsugu Freeze–Dried Hepatitis A Vaccine Containg Amino Acids and Sugars as Stabilizers, Chem Abstracts 113(2): 12106d, p. 369, col. 2 (1990).

Rowe, Plaque Assay Techniques for Murine Leukemia Viruses, Virology 42: 1136–39(1970).

Rowe, Machinery and methods in Freeze–Drying, Cyrobiology 8: 153–72(1971).

Rightsel, Freezing and Freeze–Drying of Viruses, Cryobiology 3:423–31(1967).

Phillips, A Study of Water Binding in Lyophilized Viral Vaccine Systems, Cryobiology 18: 414–19(1981).

Stamp, The Preservation of Bacteria by Drying, J Gen Microbiol 1: 251–65(1947).

Flosdorf, Procedure and Appartus for Preservation in Lyophile form of Serum and Other Biological Substances, J Immunol. 29: 389–425 (1935).

Sitch, PCT International Search Report for PCT/US94/11414, Jan. 25, 1995, 4 pages total.

Berge et. al. (1971) Appl. Microbiol. 22(5) 850–853.

Levy et. al. (1982) J. Virol. Meth. 5, 165–171.

Webster's II: New Riverside. University Dictionary (1988) Houghton Mifflin Co. Boston MA. pp. 646 & 956.

*Primary Examiner*—James Ketter
*Assistant Examiner*—Irem Yucel
*Attorney, Agent, or Firm*—Norman J. Kruse; Luann Cserr; Robert P. Blackburn

[57] ABSTRACT

Methods for preserving an infectious recombinant virus for subsequent reconstitution are provided. Within one aspect, the method comprises the steps of (a) combining an infectious recombinant virus with an aqueous solution comprising a saccharide, a high molecular weight structural additive, a buffering component and water to form an aqueous suspension, thereby stabilizing the infectious virus; (b) cooling the aqueous suspension containing the virus to a temperature below the glass transition state temperature or below the eutectic point temperature of the formulation; and (c) removing water from the cooled aqueous suspension by sublimation to form a lyophilized virus having less than 10% water by weight of the lyophilized virus, the virus being capable of infecting mammalian cells upon reconstitution.

35 Claims, 5 Drawing Sheets

METHODS FOR PRESERVING RECOMBINANT RETROVIRUSES

CROSS-REFERENCE TO RELATED APPLICATION

This is a continuation, of application Ser. No. 08/602,165 filed Feb. 16, 1996, which is a continuation of application Ser. No. 08/153,342, filed Nov. 15, 1993, which is a continuation-in-part of application Ser. No. 08/135,938, filed Oct. 12, 1993 all now abandoned.

TECHNICAL FIELD

The present invention relates generally to the methods for preserving recombinant viruses in a dried state to retain infectious activity.

BACKGROUND OF THE INVENTION

Viruses can infect all living organisms and are known to be responsible for many infectious diseases. The viral particles that cause infection consist of an outer protein coat that encapsulates a nucleic acid core. However, the viral genome does not contain sufficient information to code for all the proteins necessary for autonomous replication. In addition, viruses lack organelles and the appropriate machinery for protein synthesis and energy production. Consequently, they are completely dependent on the host cell for nucleic acid replication or protein synthesis. In general, viruses infect living cells by binding to the host membrane and injecting their genetic material into the cytoplasm. This genetic material can signal the cells to synthesize new viral components which assemble into new viral particles that exit the host cell. The subsequent release of these particles allows a new cycle of viral infection on nearby cells. Once infected, cells may be lysed or alternatively viral particles may be released from the intact cell over a period of time. In this case, the cells are said to be persistently infected and the viral genome may remain associated with the cell over a period of weeks, months or years, and potentially through many cell divisions.

This infective mechanism has made viruses important vehicles for the delivery of therapeutic "genes of interest" into host cells. However, continued viral replication and infection is usually not desirable, consequently recombinant viruses have been further modified to be replication defective. Once modified, these genes are packaged into specially engineered virus particles and introduced into host cells by infection. This method of viral-mediated gene transfer is highly efficient because viruses by their nature are capable of infecting virtually every cell in a target population. Following infection, some viruses will stably integrate their genome into chromosomes of the infected cells and result in long-term expression of recombinant genes.

The method by which recombinant viruses are used to deliver genes of therapeutic agents into specific cells of a patient is called gene therapy. Gene therapy can be used to treat those diseases which lack gene expression for a critical protein. For example, insulin-dependent diabetes results from the absence of insulin production in the body. Dwarfism results from the absence of growth hormone and hemophilia results from the absence of Factor VIII. A replication defective recombinant virus that carries the gene for insulin, growth hormone or Factor VIII can be used to deliver the absent gene to host cells, thereby reversing the disease. Recombinant viruses can also be designed as immunogenic vaccines by introducing genes that express proteins which illicit an immune response against foreign antigens. For example, a recombinant virus that expresses gp120 can be used to illicit an immune response against the protein and correspondingly against those cells in the body which express that protein. In addition, recombinant viruses can be used to carry genetic sequences that encode inhibitory factors such as antisense messages. Antisense sequences produced from the incorporated recombinant viruses bind to corresponding sequences in mRNA preventing translation of the mRNA, thereby preventing production of the undesirable protein. Recombinant viruses can be used to carry a gene that transcribes a ribozyme. Ribozymes are RNA molecules that bind to specific sequences of RNA and cleave the transcript, preventing translation of an undesirable protein. Consequently, recombinant viruses have not shown great promise in treating different diseases. However, their effectiveness depends on their ability to infect host cells and produce a therapeutic amount of the gene of interest to treat the disease.

The use of recombinant viruses to treat individuals requires that they be able to be transported and stored for long periods at a desired temperature such that infectivity and viability of the recombinant virus is retained. The difficulty of preserving the recombinant virus without the need of low temperature for storage and transport presents problems in Third World countries, which typically do not have adequate refrigeration capabilities. For example, each year in Africa, millions of children die from infectious diseases such as measles. Vaccines necessary for the prevention of these diseases cannot be distributed to the majority of these countries because refrigeration is not readily accessible.

The initial stabilization of materials in dry form to the preservation of antitoxins, antigens and bacteria (Flosodort et al., *J. Immunol.* 29:389, 1935). However, a limitation in this process included partial denaturation of proteins when dried from an aqueous state at ambient temperatures. Drying from the frozen state helped reduce this denaturation and led to efficient preservation of other biological materials including bacteria and viruses (Stamp et al., *J. Gen. Microbiol.* 1:251, 1947; Rightsel et al., *Cryobiology* 3:423, 1967; Rowe et al., *Virology* 42136, 1970; and Rowe et al., *Cryobiology* 8:153, 1971). More recently, sugars such as sucrose, raffinose, glucose and trehalose were added in various combinations as stabilizing agents prior to lyophilization of viruses. The use of sugars enhanced recovery of viable viruses, for research purposes which require that only some virus survive for later propagation.

Currently, research grade recombinant viruses are stored as liquids at low temperatures. In addition, these formulations often contain media components that are not desirable for injection into patients. Consequently, there is a need for a method preserving purified recombinant viral infectivity in a lyophilized form at elevated temperatures, and for this form to be suitable for injection into patients. The present invention fulfills these needs and further provides other advantages.

SUMMARY OF THE INVENTION

Within one aspect of the present invention, a method is provided for preserving an infectious recombinant virus for subsequent reconstitution, comprising the steps of (a) combining an infectious recombinant virus with an aqueous solution comprising a saccharide, a high molecular weight structural additive, a buffering component and water to form an aqueous suspension, thereby stabilizing the infectious virus; (b) cooling the aqueous suspension containing the virus to a temperature below the glass transition state temperature or below the eutectic point temperature of the formulation; and (c) removing water from the cooled aqueous suspension by sublimation to form a lyophilized virus having less than 10% water by weight of the lyophilized virus, the virus being capable of infecting mammalian cells upon reconstitution.

Within another aspect of the present invention, a method is provided for preserving an infectious recombinant virus for subsequent reconstitution, comprising the steps of (a) forming an aqueous suspension as described above; and (b) removing water from the aqueous suspension by evaporation at ambient temperature to form a dehydrated virus having less than 10% water by weight of the dehydrated virus, the dehydrated virus being capable of infecting mammalian cells upon reconstitution. Within preferred embodiments, the mammalian cells are human cells, and the virus, upon reconstitution with water, is suitable for administration to humans. Within certain embodiments, the aqueous solution includes one or more amino acids.

Within one embodiment of the present invention, the infectious recombinant virus is a replication defective recombinant virus. Within a preferred embodiment, the infectious recombinant virus is a recombinant retrovirus. Within still another embodiment, the infectious virus is a Sindbis virus or coronavirus.

Suitable saccharides for use within the present invention include lactose, sucrose, trehalose, maltose, fructose, inositol, glucose, mannitol, galactose, or combinations of such saccharides, including a combination of lactose and mannitol, or a combination of sucrose and mannitol. Within preferred embodiments, the concentration of the saccharide ranges from 1% to 12% by weight. Suitable high molecular weight structural additives include human serum albumin, dextran, cellulose, gelatin, hydroxyethyl-cellulose, hydroxymethyl-cellulose and povidone. Within preferred embodiments, the concentration of the high molecular weight structural additive ranges from 0.1% to 10% by weight.

Within the present invention, suitable amino acids (if present) include arginine, lysine, glycine, glutamine, glutamic acid, ornithine, serine, asparagine, aspartic acid and salts thereof. Within preferred embodiments, the concentration of the amino acid ranges from 0.1% to 10% by weight. Suitable buffering components include tromethamine, phosphate and citrate. Within a particularly preferred embodiment, the buffering component is present in a concentration effective to provide a pH of approximately 7.4 of the aqueous suspension.

Generally, the percentage of water by weight of the lyophilized or dried virus is less than 10%. Within a preferred embodiment, the percent water by weight of the lyophilized or dried virus is less than 2%.

Within still another aspect of the present invention, a method is provided for preserving an infectious recombinant retrovirus for subsequent reconstitution, comprising the steps of (a) combining an infectious recombinant retrovirus with an aqueous solution to form an aqueous suspension, the aqueous suspension including 3–4% by weight of lactose, 0.1% by weight of human serum albumin, 0.03% or less by weight of NaCl, and a concentration of tromethamine buffer effective to provide a pH of the aqueous suspension of approximately 7.4, thereby stabilizing the infectious recombinant retrovirus; (b) cooling the suspension to a temperature of from −40° C. to −45° C. to form a frozen suspension; and (c) removing water from the frozen suspension by sublimation to form a lyophilized composition having less than 2% water by weight of the lyophilized composition, the lyophilized retrovirus being capable of infecting mammalian cells upon reconstitution. Within a related aspect, the aqueous suspension includes 0.1% by weight of arginine.

Within a particularly preferred embodiment, the recombinant retrovirus is a replication defective recombinant retrovirus suitable for administration to humans upon reconstitution.

Within other aspects of the invention, a lyophilized or dehydrated replication defective recombinant virus is provided, the virus having a half-life of at least 7 days at room temperature and being capable of infecting human cells upon reconstitution. Within various embodiments, the replication defective recombinant virus has a half-life of at least 25 days at 2° C.–8° C. (refrigeration temperature), or a half-life of at least 190 days at −20° C. Within preferred embodiments, the lyophilized or dehydrated virus is suitable for administration to humans upon reconstitution.

These and other aspects of the present invention will become evident upon reference to the following detailed description and attached drawings.

BRIEF DESCRIPTION OF THE DRAWINGS

FIG. 1 is a graph demonstrating retention of viral activity upon reconstitution of a representative recombinant retrovirus lyophilized in a formulation buffer containing mannitol.

FIG. 2 is a graph demonstrating retention of viral activity upon reconstitution of a representative recombinant retrovirus lyophilized in a formulation buffer containing lactose.

FIG. 3 is a graph demonstrating retention of viral activity upon reconstitution of a representative recombinant retrovirus lyophilized in a formulation buffer containing trehalose.

FIGS. 4A–4D are representative graphs comparing stability of liquid non-lyophilized recombinant retrovirus stored at −80° C. versus lyophilized formulated recombinant retrovirus stored at −20° C., using various saccharides. For ease of comparison, the titers have been normalized.

DETAILED DESCRIPTION OF THE INVENTION

Prior to setting forth the invention, it may be helpful to an understanding thereof to set forth definitions of certain terms that will be used hereinafter. All references which have been cited herein are hereby incorporated by reference in their entirety.

"Recombinant virus" as utilized within the present invention is a virus that is capable of infecting cells and carrying at least a gene of interest. The recombinant virus may also contain a selectable marker. As used herein, recombinant virus includes virus associated with substances normally present at any stage of production or purification, including culture or chromatography media or components thereof.

"Recombinant retrovirus" as utilized within the present invention refers to a retrovirus carrying at least a gene of interest. The retrovirus may also contain a selectable marker. The recombinant retrovirus is capable of reverse transcribing its genetic material into DNA and incorporating this genetic material into a host cell's DNA upon infection.

"Buffering compound" as utilized within the present invention is a substance that functions to maintain the aqueous suspension at a desired pH.

As noted above, the present invention is directed toward a method for preserving an infectious recombinant virus for subsequent reconstitution such that the recombinant virus is capable of infecting mammalian cells upon reconstitution. The methods described can be used to preserve a variety of different viruses, including Sindbis or coronaviruses. Suitable viruses also include recombinant type C retroviruses such as gibbon ape leukemia virus, feline leukemia virus and xeno-, poly- and amphotropic murine leukemia virus (Weiss et al., *RNA Tumor Viruses*, 2d ed. 1985).

The infectious recombinant virus may be preserved in a crude or purified form. Crude recombinant virus is produced by infected cells within a bioreactor, wherein viral particles are released from the cells into the culture media. The virus may be preserved in crude form by first adding a sufficient amount of a formulation buffer to the culture media containing the recombinant virus, to form an aqueous suspension. The formulation buffer is an aqueous solution that contains a saccharide, a high molecular weight structural additive, and a buffering component in water. The aqueous solution may also contain one or more amino acids.

The recombinant virus can also be preserved in a purified form. More specifically, prior to the addition of the formulation buffer, the crude recombinant virus described above is clarified by passing it through a filter, and then concentrated, such as by a cross flow concentrating system (Filtron Technology Corp., Nortborough, Mass.). Within one embodiment, DNase is added to the concentrate to digest exogenous DNA. The digest is then diafiltrated to remove excess media components and establish the recombinant virus in a more desirable buffered solution. The diafiltrate is then passed over a Sephadex S-500 gel column and a purified recombinant virus is eluted. A sufficient amount of formulation buffer is added to this eluate to reach a desired final concentration of the constituents (see, e.g., Examples 1-4) and to minimally dilute the recombinant virus, and the aqueous suspension is then stored, preferably at -70° C. or immediately dried. As noted above, the formulation buffer is an aqueous solution that contains a saccharide, a high molecular weight structural additive, and a buffering component in water. The aqueous solution may also contain one or more amino acids.

The crude recombinant virus can also be purified by ion exchange column chromatography. This method is described in more detail in U.S. patent application Ser. No. 08/093, 436. In general, the crude recombinant virus is clarified by passing it through a filter, and the filtrate loaded onto a column containing a highly sulfonated cellulose matrix. The recombinant virus is eluted from the column in purified form by using a high salt buffer. The high salt buffer is then exchanged for a more desirable buffer by passing the eluate over a molecular exclusion column. A sufficient amount of formulation buffer is then added, as discussed above, to the purified recombinant virus and the aqueous suspension is either dried immediately or stored, preferably at -70° C.

The aqueous suspension in crude or purified form can be dried by lyophilization or evaporation at ambient temperature. Specifically, lyophilization involves the steps of cooling the aqueous suspension below the glass transition temperature or below the eutectic point temperature of the aqueous suspension, and removing water from the cooled suspension by sublimation to form a lyophilized virus. Briefly, aliquots of the formulated recombinant virus are placed into an Edwards Refrigerated Chamber (3 shelf RC3S unit) attached to a freeze dryer (Supermodulyo 12K). A multistep freeze drying procedure as described by Phillips et al. (*Cryobiology* 18:414, 1981) is used to lyophilize the formulated recombinant virus, preferably from a temperature of -40° C. to -45° C. The resulting composition contains less than 10% water by weight of the lyophilized virus. Once lyophilized, the recombinant virus is stable and may be stored at -20° C. to 25° C., as discussed in more detail below.

Within the evaporative method, water is removed from the aqueous suspension at ambient temperature by evaporation. Within one embodiment, water is removed through spray drying (EP 520,748). Within the spray drying process, the aqueous suspension is delivered into a flow of preheated gas, usually air, whereupon water rapidly evaporates from droplets of the suspension. Spray drying apparatus are available from a number of manufacturers (e.g., Drytec, Ltd., Tonbridge, England; Lab-Plant, Ltd., Huddersfield, England). Once dehydrated, the recombinant virus is stable and may be stored at -20° C. to 25° C. Within the methods described herein, the resulting moisture content of the dried or lyophilized virus may be determined through use of a Karl-Fischer apparatus (EM Science Aquastar™ VIB volumetric titrator, Cherry Hill, N.J.), or through a gravimetric method.

The aqueous solutions used for formulation, as previously described, are composed of a saccharide, high molecular weight structural additive, a buffering component, and water. The solution may also include one or more amino acids. The combination of these components act to preserve the activity of the recombinant virus upon freezing and lyophilization, or drying through evaporation. Although a preferred saccharide is lactose, other saccharides may be used, such as sucrose, mannitol, glucose, trehalose, inositol, fructose, maltose or galactose. In addition, combinations of saccharides can be used, for example, lactose and mannitol, or sucrose and mannitol. A particularly preferred concentration of lactose is 3%-4% by weight. Preferably, the concentration of the saccharide ranges from 1% to 12% by weight.

The high molecular weight structural additive aids in preventing viral aggregation during freezing and provides structural support in the lyophilized or dried state. Within the context of the present invention, structural additives are considered to be of "high molecular weight" if they are greater than 5000 m.w. A preferred high molecular weight structural additive is human serum albumin. However, other substances may also be used, such as hydroxyethyl-cellulose, hydroxymethyl-cellulose, dextran, cellulose, gelatin, or povidone. A particularly preferred concentration of human serum albumin is 0.1% by weight. Preferably, the concentration of the high molecular weight structural additive ranges from 0.1% to 10% by weight.

The amino acids, if present, function to further preserve viral infectivity upon cooling and thawing of the aqueous suspension. In addition, amino acids function to further preserve viral infectivity during sublimation of the cooled aqueous suspension and while in the lyophilized state. A preferred amino acid is arginine, but other amino acids such as lysine, ornithine, serine, glycine, glutamine, asparagine, glutamic acid or aspartic acid can also be used. A particularly preferred arginine concentration is 0.1% by weight. Preferably, the amino acid concentration ranges from 0.1% to 10% by weight.

The buffering component acts to buffer the solution by maintaining a relatively constant pH. A variety of buffers may be used, depending on the pH range desired, preferably between 7.0 and 7.8. Suitable buffers include phosphate buffer and citrate buffer. A particularly preferred pH of the recombinant virus formulation is 7.4, and a preferred buffer is tromethamine.

In addition, it is preferable that the aqueous solution contain a neutral salt which is used to adjust the final formulated recombinant retrovirus to an appropriate iso-osmotic salt concentration. Suitable neutral salts include sodium chloride, potassium chloride or magnesium chloride. A preferred salt is sodium chloride.

Aqueous solutions containing the desired concentration of the components described above may be prepared as concentrated stock solutions.

A particularly preferred method of preserving recombinant retroviruses in a lyophilized state for subsequent reconstitution comprises the steps of (a) combining an infectious recombinant retrovirus with an aqueous solution to form an aqueous suspension, the aqueous suspension including 4% by weight of lactose, 0.1% by weight of human serum albumin, 0.03% or less by weight of NaCl, 0.1% by weight of arginine, and an amount of tromethamine buffer effective to provide a pH of the aqueous suspension of approximately 7.4, thereby stabilizing the infectious recombinant retrovirus; (b) cooling the suspension to a temperature of from −40° C. to −45° C. to form a frozen suspension; and (c) removing water from the frozen suspension by sublimation to form a lyophilized composition having less than 2% water by weight of the lyophilized composition, the composition being capable of infecting mammalian cells upon reconstitution. It is preferred that the recombinant retrovirus be replication defective and suitable for administration into humans upon reconstitution.

Figure 2:
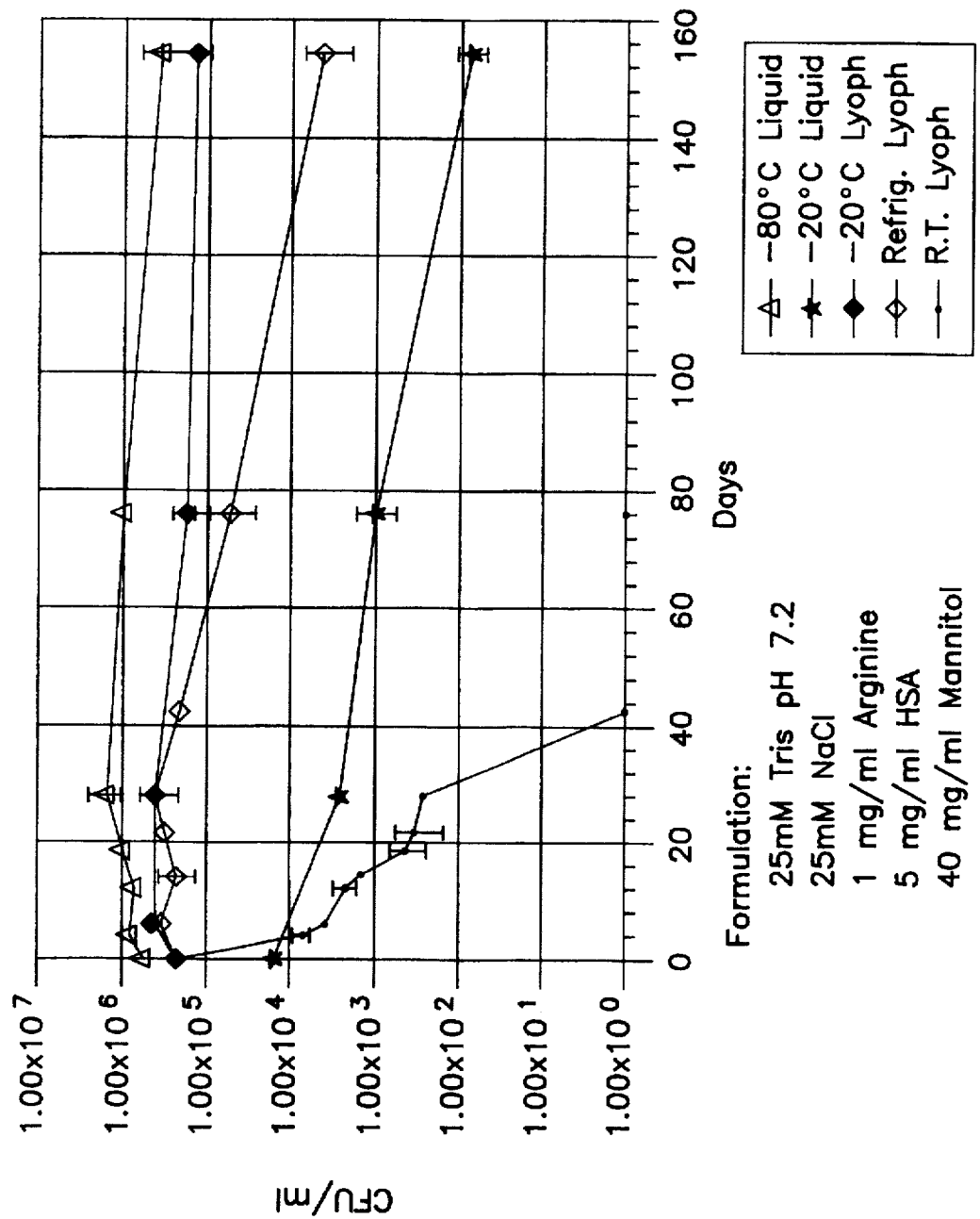
Figure 3:
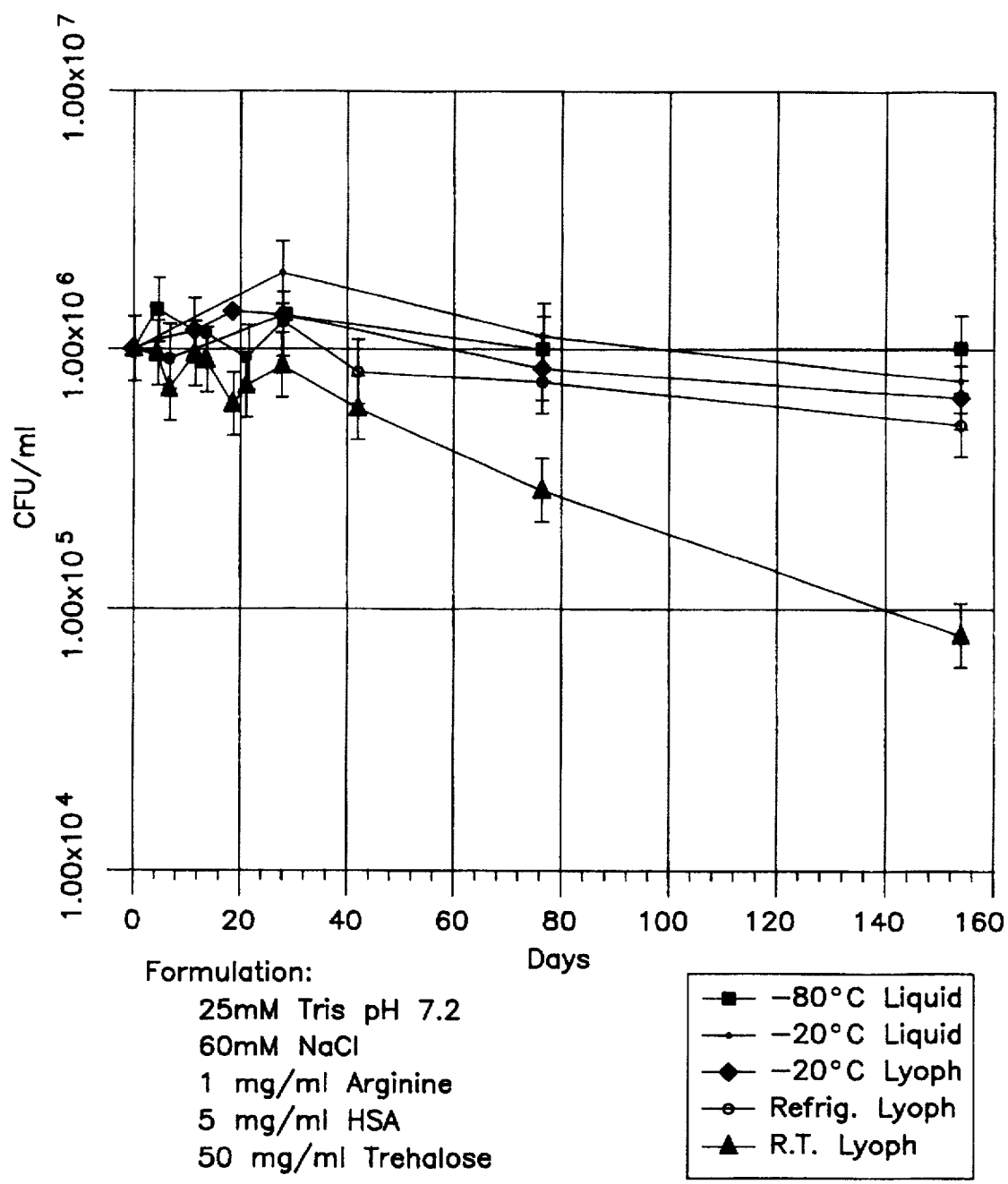
Figure 4A:
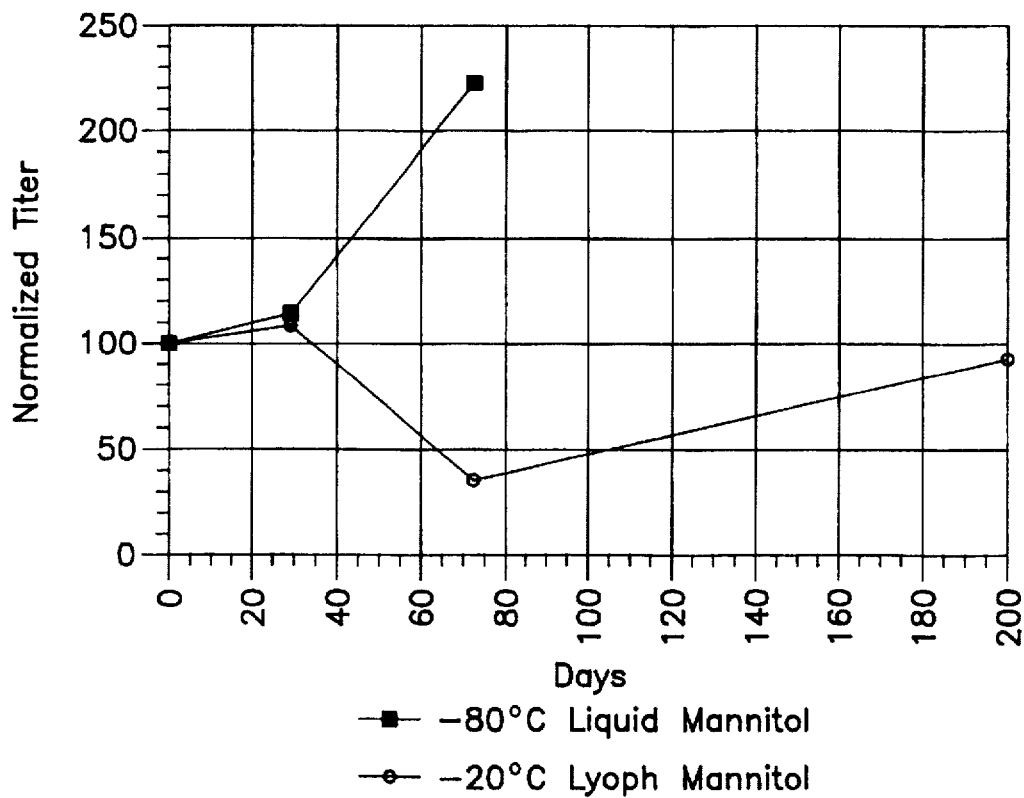
Figure 4B:
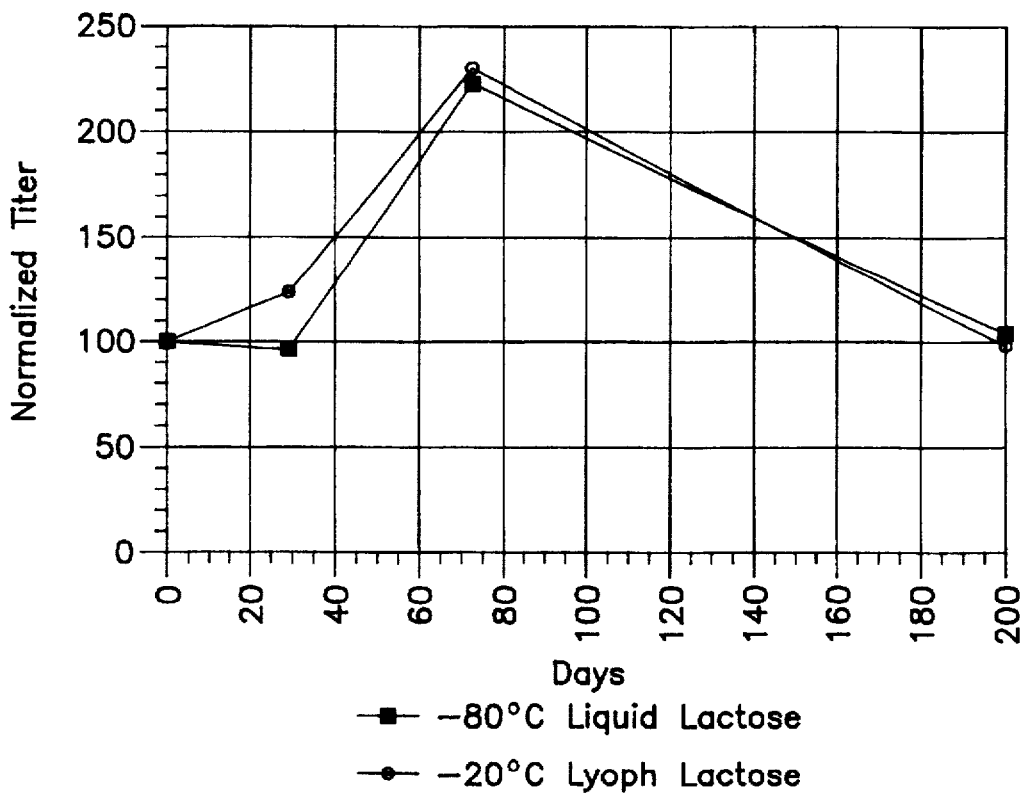
Figure 4C:
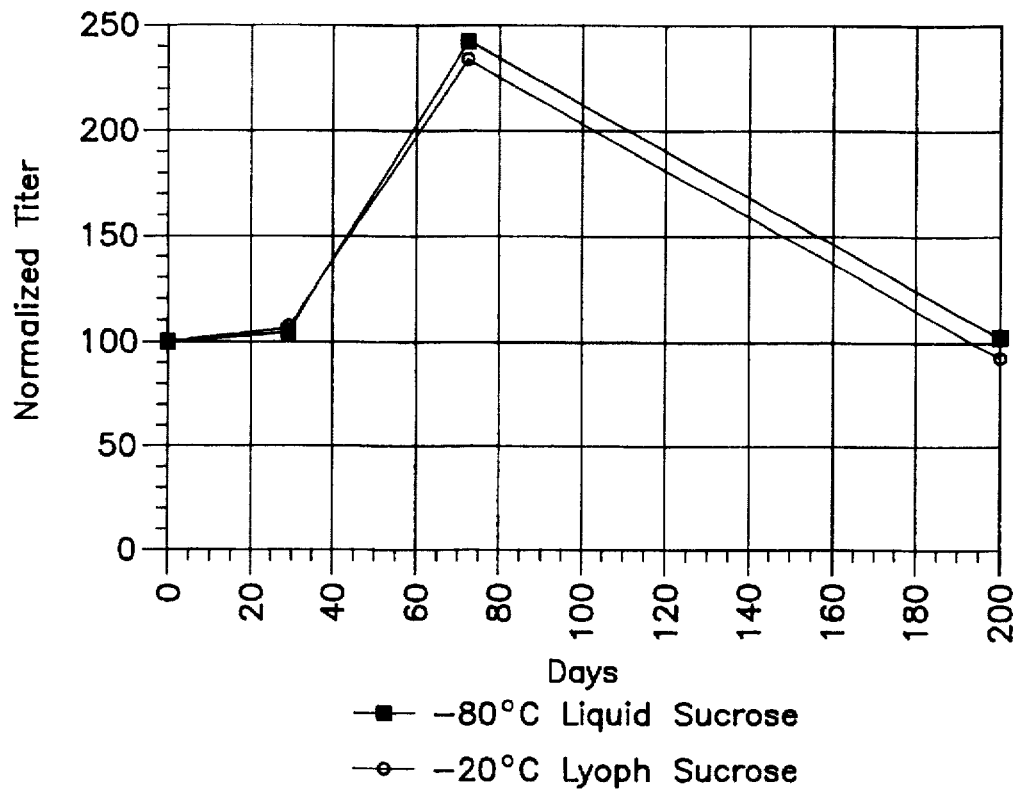
Figure 4D:
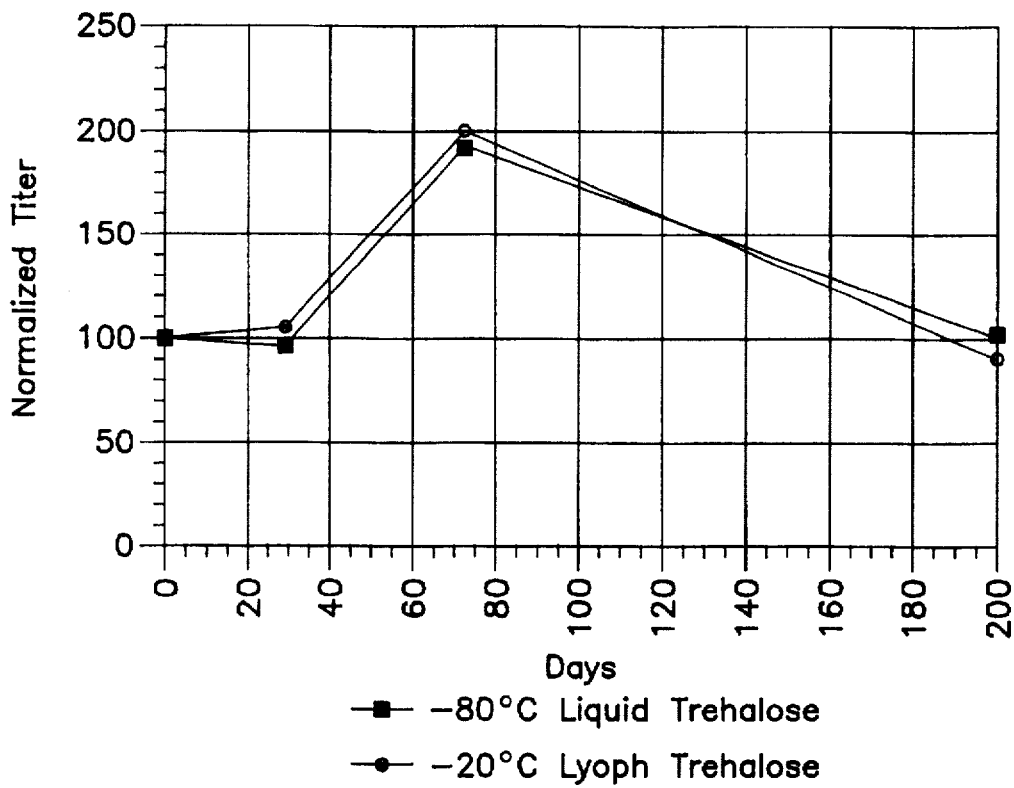

As illustrated in FIGS. 1 and 2, mannitol and lactose lyophilized recombinant retrovirus formulations were assayed for preservation of viral activity under various storage temperatures as a function of time. Similarly, FIG. 3 illustrates the results of assays of trehalose recombinant retrovirus formulations for preservation of viral activity under various storage temperatures as a function of time. FIG. 4 depicts a comparison of the viral infectivity of frozen formulated recombinant retrovirus (−80° C.) as a liquid and the viral infectivity of lyophilized recombinant retrovirus stored at −20° C. Mannitol formulations may lose considerable activity upon lyophilization (5–6 fold), but appear to remain stable subsequent to the lyophilization event. Although not preferable, such a loss is acceptable assuming sufficient amounts of virus are present in the aqueous solution.

It will be evident to those skilled in the art given the disclosure provided herein that it may be preferable to utilize certain saccharides within the aqueous solution when the lyophilized virus is intended for storage at room temperature. More specifically, it is preferable to utilize disaccharides, such as lactose or trehalose, particularly for storage at room temperature.

The lyophilized or dehydrated viruses of the subject invention may be reconstituted using a variety of substances, but are preferably reconstituted using water. In certain instances, dilute salt solutions which bring the final formulation to isotonicity may also be used. In addition, it may be advantageous to use aqueous solutions containing components known to enhance the activity of the reconstituted virus. Such components include cytokines, such as IL-2, polycations, such as protamine sulfate, or other components which enhance the transduction efficiency of the reconstituted virus. Lyophilized or dehydrated recombinant virus may be reconstituted with any convenient volume of water or the reconstituting agents noted above that allow substantial, and preferably total solubilization of the lyophilized or dehydrated sample.

The following examples are offered by way of illustration and not by way of limitation.

EXAMPLE 1

LACTOSE FORMULATION OF A RECOMBINANT RETROVIRUS

Crude recombinant retrovirus is obtained from a Celligan bioreactor (New Brunswick, New Brunswick, N.J.) containing DA cells transformed with the recombinant retrovirus (U.S. application Ser. No. 07/395,932) bound to the beads of the bioreactor matrix. The cells release the recombinant retrovirus into the growth media that is passed over the cells in a continuous flow process. The media exiting the bioreactor is collected and passed initially through a 0.8 micron filter then through a 0.65 micron filter to clarify the crude recombinant retrovirus. The filtrate is concentrated utilizing a cross flow concentrating system (Filtron, Boston, Mass.). Approximately 50 Units of DNase (Intergen, New York, N.Y.) per ml of concentrate is added to digest exogenous DNA. The digest is diafiltrated using the same cross flow system to 150 mM NaCl, 25 mM tromethamine, pH 7.2. The diafiltrate is loaded onto a Sephadex S-500 gel column (Pharmacia, Piscataway, N.J.), equilibrated in 50 mM NaCl, 25 mM tromethamine, pH 7.4. The purified recombinant retrovirus is eluted from the Sephadex S-500 gel column in 50 mM NaCl, 25 mM tromethamine, pH 7.4.

The formulation buffer containing lactose was prepared at a 2X concentrated stock solution. The formulation buffer contains 25 mM tromethamine, 70 mM NaCl, 2 mg/ml arginine, 10 mg/ml human serum albumin (HSA), and 100 mg/ml lactose in a final volume of 100 mls at a pH 7.4.

The purified recombinant retrovirus is formulated by adding one part 2X lactose formulation buffer to one part S-500 purified recombinant retrovirus. The formulated recombinant retrovirus can be stored at −70° C. to −80° C. or dried.

The formulated retrovirus is lyophilized in an Edwards Refrigerated Chamber (3 Shelf RC3S unit) attached to a Supermodulyo 12K freeze dryer (Edwards High Vacuum, Tonawanda, N.Y.). When the freeze drying cycle is completed, the vials are stoppered under a vacuum following a slight nitrogen gas bleeding. Upon removal, vials are crimped with aluminum seals.

In the given lactose study, formulated liquid product was stored at both −80° C. and at −20° C. cycling freezer. In FIG. 1, viral infectivity of these samples were compared to the viral infectivity of lyophilized samples. The lyophilized samples were stored at −20° C., refrigerator temperature and room temperature. Activity of the samples upon reconstitution are determined by titer assay.

The lyophilized recombinant retrovirus is reconstituted with 1.0 ml water. The infectivity of the reconstituted recombinant retrovirus is determined by a titer activity assay. The assay is conducted on HT 1080 human tumor cell line (ATCC CCL 121) fibroblasts or 3T3 mouse fibroblast cell line (ATCC CCL 163). Specifically, $1 \times 10^5$ cells are plated onto 6 cm plates and incubated overnight at 37° C., 10% $CO_2$. Ten microliters of a dilution series of reconstituted recombinant retroviruses are added to the cells in the presence of 4 µg/mL polybrene (Sigma, St. Louis, Mo.) and incubated overnight at 37° C., 10% $CO_2$. Following incubation, cells are selected for neomycin resistance in G418 containing media and incubated for 5 days at 37° C., 10% $CO_2$. Following initial selection, the cells are re-fed with fresh media containing G418 and incubated for 5–6 days. After final selection, the cells are stained with Commassie blue for colony detection. The titer of the sample is determined from the number of colonies, the dilution and the volume used.

FIG. 1 demonstrates that storage in lyophilized form at −20° C. to refrigerator temperatures retains similar viral activity as a recombinant retrovirus stored in liquid at −80° to −20° C. permitting less stringent temperature control during storage.

EXAMPLE 2

MANNITOL FORMULATION OF A RECOMBINANT RETROVIRUS

The recombinant retrovirus utilized in this example was purified as described in Example 1.

The formulation buffer containing mannitol was prepared as a 2X concentrated stock solution. The formulation buffer contains 25 mM tromethamine, 35 mM NaCl, 2 mg/ml arginine, 10 mg/ml HSA and 80 mg/ml mannitol at a final volume of 100 mls at a pH 7.4.

The purified recombinant retrovirus is formulated by adding one part mannitol formulation buffer to one part S-500 purified recombinant retrovirus. The formulated recombinant retrovirus can be stored at this stage at −70° C. to −80° C. or dried.

The formulated retrovirus is dried in an Edwards Refrigerated Chamber (3 Shelf RC3S unit) attached to a Supermodulyo 12K freeze dryer. When the freeze drying cycle is completed, the vials are stoppered under a vacuum following nitrogen gas bleeding to 700 mbar. Upon removal, vials are crimped with aluminum seals.

In the given mannitol study, formulated liquid product was stored at both −80° C. and at −20° C. in cycling freezers. The viral infectivity of these samples were compared to the viral infectivity of lyophilized samples, FIG. 2. The lyophilized samples were stored at −20° C., refrigerator temperature and room temperature. Activity of the samples upon reconstitution are determined using the titer assay described in Example 1.

FIG. 2 demonstrates that storage in lyophilized form at −20° C. to refrigerator temperature retains significant viral activity as compared to recombinant retrovirus stored in liquid at −80° C. or −20° C., permitting less stringent temperature control during storage.

EXAMPLE 3

TREHALOSE FORMULATION OF A RECOMBINANT RETROVIRUS

The recombinant retrovirus utilized in this example was purified as described in Example 1.

The formulation buffer containing trehalose was prepared as a 2X concentrated stock solution. The formulation buffer contains 25 mM tromethamine, 70 mM NaCl, 2.0 mg/ml arginine, 10.0 mg/ml HSA and 100 mg/ml trehalose at a final volume of 100 mls at a pH 7.2.

The purified recombinant retrovirus is formulated by adding one part trehalose formulation buffer to one part S-500 purified recombinant retrovirus. The formulated recombinant retrovirus can be stored at this stage at −70° C. to −80° C. or dried.

The formulated retrovirus is dried in an Edwards Refrigerated Chamber (3 Shelf RC3S unit) attached to a Supermodulyo 12K freeze dryer. When the freeze drying cycle is completed, the vials are stoppered under a vacuum following nitrogen gas bleeding to 700 mbar. Upon removal, vials are crimped with aluminum seals.

In the given trehalose study, formulated liquid product was stored at both −80° C. and at −20° C. in cycling freezers. The viral infectivity of these samples was compared to the viral infectivity of lyophilized samples, FIG. 3. The lyophilized samples were stored at −20° C., refrigerator temperature and room temperature. Activity of the samples upon reconstitution are determined using the titer assay as described in Example 1.

FIG. 3 demonstrates that storage in lyophilized form at −20° C. to refrigerator temperature retains similar viral activity as compared to recombinant retrovirus stored in liquid at −80° C. to −20° C. permitting less stringent temperature control during storage.

Viral infectivity of liquid formulated recombinant retrovirus samples stored at −80° C. was compared to viral infectivity of lyophilized formulated recombinant retrovirus stored at −20° C. Initially, a bulk of recombinant retrovirus was received and formulated in four different ways as shown below. The formulated recombinant retrovirus was then frozen in bulk for 1.5 months subsequent to being quick thawed and freeze dried. Positive controls were stored at −80° C. for comparison with lyophilized samples which were stored at −20° C. after freeze-drying. The formulations are listed below:

| Formulation | Sugar Concentration (mg/ml) | Buffer Concentration (mM tromehamine) | Salt Concentration (mM NaCl) | Arginine Concentration (mg/ml) | Human Serum Albumin Concentration (mg/ml) |
|---|---|---|---|---|---|
| Mannitol | 40 | 25 | 25 | 1 | 5 |
| Lactose | 40 | 25 | 75 | 1 | 5 |
| Sucrose | 50 | 25 | 60 | 1 | 5 |
| Trehalose | 50 | 25 | 60 | 1 | 5 |

In the graphs of FIG. 4, the y-axis on each of the 4 graphs (A, B, C, D) represent the normalized titer. At an initial time point after lyophilization, +=0, a titer value was established for both the −80° C. liquid sample and the −20° C. lyophilized sample. At each time point of the stability study, the titer obtained was divided by the zero time point titer value and the % of original entered onto the graph.

The data demonstrates that post-lyphilization activity is maintained in the lyophilized sample (stored at −20° C.) relative to the liquid sample (stored at −80° C.). The formulated lyophilized recombinant retrovirus was stored in a −20° C. freezer (a frost-free cycling freezer). Comparison to the formulated liquid recombinant retrovirus stored at −80° C. indicates the lyophilized form permits less stringent control of storage conditions.

We claim:

1. A method for preserving a purified infectious recombinant retrovirus for subsequent reconstitution, comprising:

(a) combining a purified infectious recombinant retrovirus with an aqueous solution comprising a saccharide, a high molecular weight structural additive, an amino acid, a buffering component and water to form an aqueous suspension, thereby stabilizing the infectious retrovirus;

(b) cooling the aqueous suspension containing the retrovirus to a temperature below the glass transition state temperature or below the eutectic point temperature of the formulation; and (c) removing water from the cooled aqueous suspension by sublimation to form lyophilized retrovirus having less than 10% water by weight of the lyophilized retrovirus, which lyophilized retrovirus can infect mammalian cells upon reconstitution.

2. A method for preserving a purified infectious recombinant retrovirus for subsequent reconstitution, comprising:

(a) combining a purified infectious recombinant retrovirus with an aqueous solution comprising a saccharide, a high molecular weight structural additive, an amino acid, a buffering component and water to form an aqueous suspension, thereby stabilizing the infectious retrovirus; and (b) removing water from the aqueous suspension by evaporation at ambient temperature to form a dehydrated retrovirus having less than 10% water by weight of the dehydrated retrovirus, which dehydrated retrovirus can infect mammalian cells upon reconstitution.

3. A method for preserving a purified infectious recombinant retrovirus for subsequent reconstitution, comprising:

(a) combining a purified infectious recombinant retrovirus with an aqueous solution comprising a saccharide, a high molecular weight structural additive, a buffering component and water to form an aqueous suspension, thereby stabilizing the infectious retrovirus;

(b) cooling the aqueous suspension containing the retrovirus to a temperature below the glass transition state temperature or below the eutectic point temperature of the formulation; and (c) removing water from the cooled aqueous suspension by sublimation to form lyophilized retrovirus having less than 10% water by weight of the lyophilized retrovirus, which lyophilized retrovirus can infect mammalian cells upon reconstitution.

4. A method for preserving a purified infectious recombinant retrovirus for subsequent reconstitution, comprising:

(a) combining a purified infectious recombinant retrovirus with an aqueous solution comprising a saccharide, a high molecular weight structural additive, a buffering component and water to form an aqueous suspension, thereby stabilizing the infectious retrovirus; and (b) removing water from the aqueous suspension by evaporation at ambient temperature to form a dehydrated retrovirus having less than 10% water by weight of which dehydrated retrovirus, the dehydrated retrovirus can infect mammalian cells upon reconstitution.

5. The method of any of claims 1, 2, 3, or 4 wherein the infectious recombinant retrovirus is replication defective.

6. The method of any of claims 1, 2, 3, or 4 wherein the saccharide is selected from the group consisting of sucrose, trehalose, maltose, fructose, inositol, glucose, mannitol and galactose.

7. The method of any of claims 1, 2, 3, or 4 wherein the saccharide is lactose.

8. The method of any of claims 1, 2, 3, or 4 wherein the high molecular weight structural additive is selected from the group consisting of dextran, cellulose, gelatin, hydroxyethyl-cellulose, hydroxymethyl-cellulose and povidone.

9. The method of any of claims 1, 2, 3, or 4 wherein the high molecular weight structural additive is human serum albumin.

10. The method of claims 1 or 2 wherein the amino acid is selected from the group consisting of lysine, glycine, glutamine, glutamic acid, ornithine, serine, asparagine, aspartic acid and salts thereof.

11. The method of claims 1 or 2 wherein the amino acid is arginine or a salt of arginine.

12. The method of any of claims 1, 2, 3, or 4 wherein the buffering component is selected from the group consisting of phosphate and citrate.

13. The method of any of claims 1, 2, 3, or 4 wherein the buffering component, is tromethamine.

14. The method of any of claims 1, 2, 3, or 4 wherein the percent water by weight of the lyophilized or dried retrovirus is less than 8%.

15. The method of any of claims 1, 2, 3, or 4 wherein the percent water by weight of the lyophilized or dried retrovirus is less than 2%.

16. The method of any of claims 1, 2, 3, or 4 wherein the saccharide is present at a concentration from 1% to 12% by weight of the aqueous suspension.

17. The method of any of claims 1, 2, 3, or 4 wherein the saccharide is a mixture of mannitol and lactose.

18. The method of any of claims 1, 2, 3, or 4 wherein the saccharide is a mixture of mannitol and sucrose.

19. The method of any of claims 1, 2, 3, or 4 wherein the high molecular weight structural additive is present at a concentration from 0.1% to 10% by weight of the aqueous suspension.

20. The method of any of claims 1, 2, 3, or 4 wherein the amino acid is present at a concentration from 0.1% to 10% by weight of the aqueous suspension.

21. The method of any of claims 1, 2, 3, or 4 wherein the buffering component is present at a concentration effective to provide a pH of approximately 7.4 of the aqueous suspension.

22. The method of any of claims 1, 2, 3, or 4 wherein the mammalian cells are human cells.

23. A method for preserving a purified infectious recombinant retrovirus for subsequent reconstitution, comprising:

(a) combining a purified infectious recombinant retrovirus with an aqueous solution to form an aqueous suspension, the aqueous suspension being 3%–4% by weight of lactose, 0.1% by weight of human serum albumin, 0.03% or less by weight of NaCl, 0.1% by weight of arginine, and an amount of tromethamine buffer effective to provide a pH of the aqueous suspension of approximately 7.4 and water, thereby stabilizing the infectious recombinant retrovirus;

(b) cooling the aqueous suspension to a temperature of from −40° C. to −45° C. to form a frozen suspension; and (c) removing water from the frozen suspension by sublimation to form a lyophilized composition having less than 2% water by weight of the lyophilized composition, which lyophilized retrovirus can effect mammalian cells upon reconstitution.

24. A method for preserving a purified infectious recombinant retrovirus for subsequent reconstitution, comprising:

(a) combining a purified infectious recombinant retrovirus with an aqueous solution to form an aqueous suspension, the aqueous suspension being 3%–4% by weight of lactose, 0.1% by weight of human serum albumin, 0.03% or less by weight of NaCl, and an amount of tromethamine buffer effective to provide a: pH of the aqueous suspension of approximately 7.4 and water, thereby stabilizing the infectious recombinant retrovirus;

(b) cooling the aqueous suspension to a temperature of from −40° C. to −45° C. to form a frozen suspension; and (c) removing water from the frozen suspension by sublimation to form a lyophilized composition having less than 2% water by weight of the lyophilized composition, which lyophilized retrovirus can infect mammalian cells upon reconstitution.

25. The method of claims 23 or 24 wherein the recombinant retrovirus is replication defective.

26. The method of claims 23 or 24 wherein lactose is present at a concentration from 30 to 40 mg/ml and mannitol is present at a concentration from 5 to 10 mg/ml of the aqueous suspension.

27. The method of claims 23 or 24 wherein sucrose is present at a concentration from 30 to 40 mg/ml and mannitol is present at a concentration from 5 to 10 mg/ml of the aqueous suspension.

28. The method of claims 23 or 24 wherein the mammalian cells are human cells.

29. A lyophilized replication defective recombinant retrovirus having a half-life at room temperature of at least seven days and can infect human cells upon reconstitution.

30. A lyophilized replication defective recombinant retrovirus having a half-life at a temperature of 2° C. to 8° C. of at least 25 days and can infect human cells upon reconstitution.

31. A lyophilized replication defective recombinant retrovirus having a half-life at $-20°$ C. of at least 190 days and can infect human cells upon reconstitution.

32. The lyophilized retrovirus of any of claims 29, 30 or 31 wherein the retrovirus is suitable for administration to humans upon reconstitution.

33. A dehydrated replication defective recombinant retrovirus having a half-life at room temperature of at least seven days and can infect human cells upon reconstitution.

34. A dehydrated replication defective recombinant retrovirus having a half-life at a temperature of 2° C. to 8° C. of at least 25 days and can infect human cells upon reconstitution.

35. A dehydrated replication defective recombinant retrovirus having a half-life at $-20°$ C. of at least 190 days and can infect human cells upon reconstitution.

* * * * *

UNITED STATES PATENT AND TRADEMARK OFFICE
CERTIFICATE OF CORRECTION

PATENT NO. : 5,792,643

DATED : August 11, 1998

INVENTOR(S) : Herrmann, et al.

Page 1 of 2

It is certified that error appears in the above-identified patent and that said Letters Patent is hereby corrected as shown below:

Column 4, line 29, after "mannitol." insert --The composition of the formulation buffer was 25mM Tris, pH 7.2, 60 mM NaCl, 1 mg/ml Arginine, 5 mg/ml HSA, 50 mg/ml lactose.--

Column 4, line 32, after "lactose." insert --The composition of the formulation buffer was 25 mM Tris, pH 7.2, 25 mM NaCl, 1 mg/ml Arginine, 5 mg/ml HSA, 40 mg/ml Mannitol.--

Column 4, line 35, after "trehalose." insert --The composition of the formulation buffer was 25 mM Tris, pH 7.2, 60 mM NaCl, 1 mg/ml Arginine, 5 mg/ml HSA, 50 mg/ml Trehalose.--

Column 13, line 4, after "retrovirus" insert --which--.
Column 13, line 18, after "and" insert --which--.
Column 13, line 21, after "and" insert --which--.
Column 14, line 2, after "and" insert --which--.
Column 14, line 14, after "and" insert --which--.
Column 14, line 17, after "and" insert --which--.

UNITED STATES PATENT AND TRADEMARK OFFICE
CERTIFICATE OF CORRECTION

PATENT NO.  : 5,792,643
DATED       : August 11, 1998
INVENTOR(S) : Hermann, et al.

It is certified that error appears in the above-identified patent and that said Letters Patent is hereby corrected as shown below:

Col. 14, line 10, after "and" insert --which--.

Signed and Sealed this

Twenty-third Day of February, 1999

Attest:

Q. TODD DICKINSON

Attesting Officer    Acting Commissioner of Patents and Trademarks